US011642138B2

(12) United States Patent
Petteys et al.

(10) Patent No.: US 11,642,138 B2
(45) Date of Patent: May 9, 2023

(54) PATELLA CLAMP

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Timothy J. Petteys, Bartlett, TN (US); Roger Ryan Dees, Jr., Drummonds, TN (US); Randy C. Winebarger, Southhaven, MS (US)

(73) Assignees: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

( * ) Notice: Subject to any disclaimer, the term of this patent is extended or adjusted under 35 U.S.C. 154(b) by 42 days.

(21) Appl. No.: 17/338,091

(22) Filed: Jun. 3, 2021

(65) Prior Publication Data

US 2021/0378683 A1  Dec. 9, 2021

Related U.S. Application Data

(60) Provisional application No. 63/035,015, filed on Jun. 5, 2020.

(51) Int. Cl.
*A61B 17/15* (2006.01)
*A61B 17/00* (2006.01)

(52) U.S. Cl.
CPC .... *A61B 17/158* (2013.01); *A61B 2017/0042* (2013.01); *A61B 2017/00407* (2013.01)

(58) Field of Classification Search
CPC .............. A61B 17/158; A61B 17/1677; A61B 17/1767
See application file for complete search history.

(56) References Cited

U.S. PATENT DOCUMENTS 5,147,365 A * 9/1992 Whitlock ............. A61B 17/158
606/88
5,716,362 A * 2/1998 Treacy ............... A61B 17/1677
606/88

(Continued)

OTHER PUBLICATIONS

Resurfacing Patellar Preparation, Technique Guide, Smith & Nephew, Inc., (2010).

*Primary Examiner* — Matthew J Lawson
(74) *Attorney, Agent, or Firm* — KDW Firm PLLC (57) ABSTRACT

Disclosed herein is a patella clamp configured to grip a patient's patella. The patella clamp includes a clamping assembly, a ratchet arm assembly, and a handle assembly. The clamping assembly includes first and second patella grip portions mounted in opposing relationship. In use, actuation of the handle assembly moves the second patella grip portion towards the first patella grip portion to clamp the patient's patella. The handle assembly is configured to be moveably adjustable (e.g., rotatable) relative to the clamping assembly. For example, each of the first and second patella grip portions are coupled to mating features mounted on the ratchet arm assembly. Decoupling of the mating features allows the first and second patella grip portions to rotate about the longitudinal axis of the ratchet arm assembly. Thus arranged, the patella clamp is configured to enable the surgeon to reposition the handle assembly to provide increased visibility, etc.

20 Claims, 7 Drawing Sheets

(56) References Cited

U.S. PATENT DOCUMENTS

| | | | | |
|---|---|---|---|---|
| 7,566,335 B1* | 7/2009 | Scott | ............ | A61B 17/158 606/88 |
| 8,951,262 B2* | 2/2015 | Kecman | ............ | A61B 17/1767 606/99 |
| 2003/0163137 A1* | 8/2003 | Smucker | ............ | A61B 17/1767 606/87 |
| 2004/0162561 A1* | 8/2004 | Marchyn | ............ | A61B 17/1677 606/78 |
| 2006/0142777 A1* | 6/2006 | Bastian | ............ | A61B 17/158 606/88 |
| 2008/0177394 A1* | 7/2008 | Chauhan | ............ | A61B 17/1677 623/20.18 |
| 2012/0101505 A1* | 4/2012 | Claypool | ............ | A61B 17/158 606/88 |
| 2013/0035693 A1* | 2/2013 | Wright | ............ | A61B 17/158 606/88 |
| 2013/0079784 A1* | 3/2013 | Vail | ............ | A61B 17/158 606/88 |
| 2013/0184712 A1* | 7/2013 | Choong | ............ | A61B 17/158 606/88 |
| 2013/0338672 A1* | 12/2013 | Harris | ............ | A61B 17/1767 606/88 |

* cited by examiner

PATELLA CLAMP

CROSS-REFERENCE TO RELATED APPLICATIONS

This is a non-provisional of, and claims the benefit of the filing date of, U.S. provisional patent application No. 63/035,015, filed Jun. 5, 2020, entitled "Patella Clamp," the entirety of which application is incorporated by reference herein.

TECHNICAL FIELD

The present disclosure is directed to an orthopedic surgical instrument, and more specifically to a patella clamp including a handle assembly and a clamping assembly, wherein the handle assembly is moveably adjustable relative to the clamping assembly.

BACKGROUND

Orthopedic patella clamps are known. Generally speaking, a patella clamp includes a handle assembly and a clamping or resection assembly (terms used interchangeably herein without the intent to limit). In use, the clamping assembly may include first and second grip portions for engaging a patient's patella positioned therebetween. In one embodiment, the first and second grip portions may engage the patient's patella in the superior/inferior direction and the handle assembly may include, for example, a threaded shaft and nut for moving the first and second grip portions. Alternatively, the first and second grip portions may engage the patient's patella in the medial/lateral direction and the handle assembly may include, for example, a pistol grip.

In either event, one disadvantage of known patella clamps is that the clamping assembly and the handle assembly remain in the same position with respect to each other. That is, the handle assembly is not adjustable relative to the clamping assembly. Having the position of the handle assembly fixed with respect to the clamping assembly limits the opportunity of use by a surgeon.

It would be beneficial to provide a lightweight adjustable patella clamp that allows increased visibility when resecting a patient's patella. For example, by arranging the patella clamp so that the clamping assembly and the handle assembly can be moveably adjustable relative to each other, the patella clamp may accommodate variations in subluxation or degrees of eversion surgical techniques as well as left and right knees and medial versus lateral approaches.

Accordingly, there remains a need for an improved patella clamp. It is with this in mind that the present disclosure is provided.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

Disclosed herein is a patella clamp including a clamping assembly and a handle assembly. In use, the clamping assembly is arranged and configured to grip a patient's patella. In accordance with one or more features of the present disclosure, the handle assembly is arranged and configured to be moveably adjustable relative to the clamping assembly. For example, in one embodiment, the clamping assembly is coupled to the handle assembly via a multi-positional ratcheting assembly (e.g., an adjustable ratchet assembly) so that the handle assembly can be rotated relative to the clamping assembly. In one embodiment, the ratchet assembly may include a series of ball plungers and/or springs. Thus arranged, in use, the patella clamp is arranged and configured to enable the surgeon to reposition (e.g., move, rotate, etc.) the handle assembly out of the way to enable, for example, increased visibility and/or to accommodate other anatomy.

In one embodiment, the handle assembly is arranged and configured to be ratcheted relative to the clamping assembly.

In one embodiment, the patella clamp is arranged to couple, hold, engage, etc. the patient's patella superiorly/inferiorly or medially/laterally by adjusting the position of the handle assembly relative to the clamping assembly.

In one embodiment, the handle assembly may be adjusted relative to the clamping assembly prior to engaging the patient's patella. Alternatively, in one embodiment, the handle assembly may be adjusted relative to the clamping assembly after engaging the patient's patella.

In one embodiment, the clamping assembly includes a saw blade slot arranged and configured to receive a saw blade therethrough for resecting a portion of the patient's patella. In one embodiment, the saw blade slot may extend circumferentially about the damping assembly in almost 270 degrees.

In one embodiment, the clamping assembly can either pull or push for gripping the patella.

In one embodiment, the clamping assembly includes a resection height stylus arranged and configured to control or measure an amount of bone to be resected and/or an amount of patella bone remaining.

In one embodiment, the clamping assembly may be arranged and configured to receive a reamer guide. For example, in one embodiment, the clamping assembly may include one or more connection mechanisms for attaching, engaging etc. a reamer guide.

In one embodiment, the patella clamp comprises a first patella grip portion, a second patella grip portion mountable on the first patella grip portion in an opposing relative moving relationship, a ratchet arm having a first end portion, a second end portion and a longitudinal axis, the second end portion having a first engagement element mounted thereon, a bushing mounted over the second end portion of the ratchet arm, wherein the bushing is capable of rotating around the ratchet arm and is also coupled to the first patella grip portion, and a second engagement element mounted over the second end portion of the ratchet arm and coupled to the second patella grip portion, wherein decoupling of the first and second engagement elements allows the first and second patella grip portions to rotate about the longitudinal axis of the ratchet arm.

In some embodiments, the first and second engagement portions may include male and female protrusions and recesses, a Hirth coupling, ball plungers, a spline joint, or any other arrangement that allows for selective engagement and rotation of the first and second engagement elements.

In some embodiments, the patella clamp may further include a lever mountable over the ratchet arm to urge the first patella grip portion and the second patella grip portions together. Additionally, the lever may be actuated by movement of a handle assembly such as, for example, a trigger and handle assembly. The lever may also be biased to provide resistance to the trigger. In additional embodiments, the handle may further include a proximal portion and a distal portion, the proximal portion housing the ratchet arm assembly. In an additional embodiment, the ratchet arm may further include a biasing element to push the first grip portion and the second patella grip portion apart.

In further embodiments, the ratchet arm may include teeth, the teeth capable of being engaged with a lock button. The lock button may hold the first patella grip portion and the second patella grip portion in fixed relationship. The lock button may be biased to engage the teeth on the ratchet arm. In use, releasing of the lock button (e.g., depressing the lock button) disengages the lock button from the ratchet arm so that the second patella grip portion may be moved relative to the first patella grip portion in a non-clamping direction to, for example, release the patient's patella from in-between the first and second patella grip portions.

In a further embodiment, the first patella grip portion includes slots for receiving a sawblade. Additionally, the patella clamp may be provided with a resection height stylus mountable to the clamp and capable of adjusting the depth of patella resection. The resection height stylus may further be provided with indicia. Additionally, the patella clamp may be provided with a reamer guide mountable to the clamp and capable of adjusting the location, orientation or depth of reaming.

In one embodiment, a patella clamp is disclosed. The patella clamp including a clamping assembly including first and second patella grip portions, a handle assembly including first and second arms, and a ratchet arm assembly arranged and configured to couple the handle assembly to the clamping assembly so that actuation of the handle assembly is transferred to the clamping assembly to secure a patient's patella between the first and second patella grip portions. The ratchet arm assembly is arranged and configured to enable the handle assembly to be rotatable about a longitudinal of the ratchet arm assembly so that a position of the handle assembly can be adjusted relative to the clamping assembly.

In one embodiment, the ratchet arm assembly includes a ratchet arm having a first end operably associated with the handle assembly and a second end operably associated with the clamping assembly and a first engagement element coupled to the second end, the first engagement element being non-rotatably coupled to the ratchet arm, wherein the second patella grip portion includes a second engagement element selectively engageable with the first engagement element.

In one embodiment, in use, separating the second engagement element from the first engagement element enables the clamping assembly to be rotate relative to the handle assembly.

In one embodiment, the ratchet arm assembly further includes a bushing moveably coupled to the ratchet arm, the bushing operably coupled to the first patella grip portion to moveably couple the first patella grip portion to the ratchet arm.

In one embodiment, the ratchet arm assembly further includes a fastener passing through a bore formed in the second engagement element and into threaded engagement with a threaded bore formed in the first engagement element to couple the second engagement element and the second patella grip portion to the ratchet arm.

In one embodiment, the ratchet arm assembly further includes a biasing element positioned between a head of the fastener and the second engagement element, the biasing element arranged and configured to bias the second engagement element into contact with the first engagement element.

In one embodiment, the first and second engagement elements each include a mating surface and a mating feature arranged and configured to engage a mating feature of the other engagement element.

In one embodiment, the mating features includes a plurality of corresponding male protrusions and female recesses arranged and configured to mate with each other.

In one embodiment, the ratchet arm further includes a plurality of teeth positioned between the first and second ends, the ratchet arm assembly including a lever operably associated with the handle assembly such that actuation of the handle assembly causes the lever to interact with the teeth to move the ratchet arm distally to move the first and second patella grip portions relative to each other.

In one embodiment, the patella clamp further includes a lock button arranged and configured to interact with the teeth formed on the ratchet arm to fix a position of the second patella grip portion relative to the first patella grip portion.

In one embodiment, the clamping assembly is also arranged and configured to be angulated relative to a longitudinal axis of the ratchet arm.

In one embodiment, the first and second patella grip portions are arranged and configured in opposing mating relationship, the first patella grip portion being stationary, the second patella grip portion being moveable so that actuation of the handle assembly moves the second patella grip portion towards the first patella grip portion.

In one embodiment, the handle assembly includes a first arm and a second arm pivotably coupled to the first arm so that movement of the second arm relative to the first arm actuates the handle assembly.

In one embodiment, in an opened, non-actuated position, the first and second patella grip portions are spaced by 60 mm.

In one embodiment, the first patella grip portion includes a cutting slot formed in a perimeter thereof, for receiving a sawblade.

In one embodiment, the patella clamp further includes a resection height stylus releasably coupled to the second patella grip portion, the resection height stylus being arranged and configured to measure an amount of a patient's bone to be resected.

In one embodiment, the resection height stylus includes a knob, a resection body including a bore formed therein, a paddle arranged and configured to contact a patient's patella, and a bolt arranged and configured to pass through the bore formed in the resection body and into threaded engagement with the knob, the bolt being coupled to the paddle, in use, rotation of the knob adjusts a position of the paddle relative to the resection body.

In one embodiment, the patella clamp further includes a patella reamer guide arranged and configured to receive and guide a reamer, the patella reamer guide being releasably coupled to the first patella grip portion.

In one embodiment, a patella clamp is disclosed. The patella clamp includes a clamping assembly including first and second patella grip portions, a handle assembly including first and second arms, a ratchet arm assembly arranged and configured to couple the handle assembly to the clamping assembly so that actuation of the handle assembly is transferred to the clamping assembly to move the second patella grip portion relative to the first patella grip portion to secure a patient's patella between the first and second patella grip portions, and means for rotatably adjusting the handle assembly relative to the clamping assembly.

In one embodiment, the ratchet arm assembly includes a ratchet arm having a first end operably associated with the handle assembly and a second end operably associated with the clamping assembly and the means for rotatably adjusting the handle assembly relative to the clamping assembly includes a first engagement element coupled to the second end, the first engagement element being non-rotatably coupled to the ratchet arm, and a second engagement element operably associated with the second patella grip portion, the second engagement element selectively engageable with the first engagement element, wherein, in use, separating the second engagement element from the first engagement element enables the clamping assembly to be rotate relative to the handle assembly.

Embodiments of the present disclosure provide numerous advantages. In one non-limiting example advantage, the clamping assembly (e.g., first and second patella grip portions) of a patella clamp may be rotated relative to a handle assembly. This allows for the handle assembly to be moved out of the way during examination, evaluation, and/or resection of the patella. Thus arranged, increased visibility may be provided (e.g., a surgeon can see the patella better). In addition, an increased working window can be created enabling a surgeon to utilize a resection tool and/or a reaming guide without interference from the handle assembly. Furthermore, the patella may be gripped with the patella in a wider variety of positions. A further advantage is that the clamp of the present disclosure may ratchet the patella grip portions with the handle in a variety of positions. In an additional non-limiting example advantage, the clamp of the present disclosure has a larger opening that may grip on all patellae, allowing fewer instruments to be needed.

Further features and advantages of at least some of the embodiments of the present invention, as well as the structure and operation of various embodiments of the present invention, are described in detail below with reference to the accompanying drawings.

BRIEF DESCRIPTION OF THE DRAWINGS

By way of example, a specific embodiment of the disclosed device will now be described, with reference to the accompanying drawings, in which.

It should be understood that the drawings are not necessarily to scale and that the disclosed embodiments are sometimes illustrated diagrammatically and in partial views. In certain instances, details which are not necessary for an understanding of the disclosed methods and devices or which render other details difficult to perceive may have been omitted. It should be further understood that this disclosure is not limited to the particular embodiments illustrated herein. In the drawings, like numbers refer to like elements throughout unless otherwise noted.

DETAILED DESCRIPTION

Various features or the like of an orthopedic patella clamp arranged and configured to enable adjustability between the clamping assembly and the handle assembly will now be described more fully hereinafter with reference to the accompanying drawings, in which one or more features of the patella clamp will be shown and described. It should be appreciated that the various features may be used independently of, or in combination, with each other. It will be appreciated that a patella clamp as disclosed herein may be embodied in many different forms and should not be construed as being limited to the embodiments set forth herein. Rather, these embodiments are provided so that this disclosure will convey certain features of the patella clamp to those skilled in the art.

As will be described herein, in accordance with one or more features of the present disclosure, the patella clamp includes a clamping or gripping assembly (terms used interchangeably without the intent to limit) arranged and configured to grip a patient's patella and a handle assembly, a trigger, an arm assembly, a pistol grip, etc. (terms used interchangeably herein without the intent to limit) arranged and configured to adjust, move, etc. the clamping assembly about the patient's patella. In use, the clamping assembly is arranged and configured to be moveable adjustable relative to the handle assembly. For example, in one embodiment, the clamping assembly may be arranged and configured to rotate about a longitudinal axis so that, in use, the handle assembly can be rotated to provide increased visibility and/or an increased working space.

Figure 1:
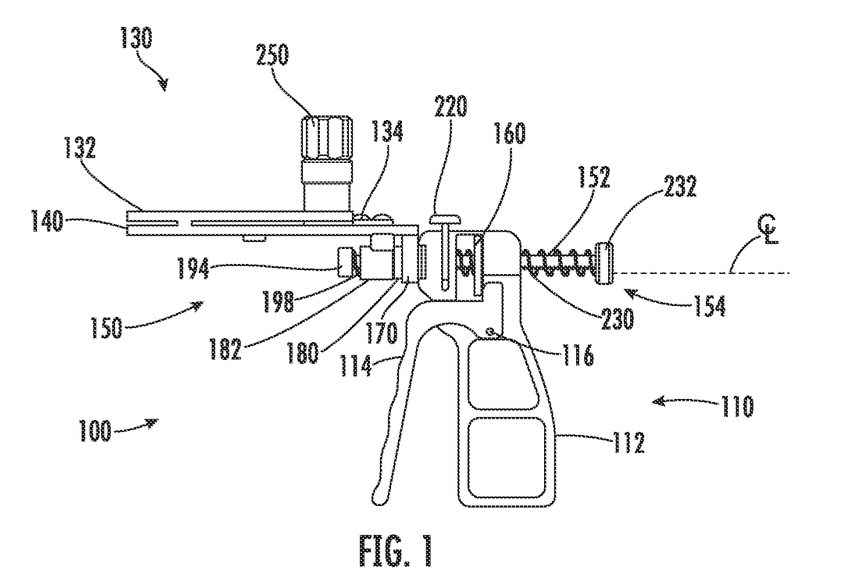
FIG. 1 illustrates a side view of an embodiment of a patella clamp in accordance with one or more features of the present disclosure, the patella clamp including a handle assembly, a clamping assembly, and a ratchet arm assembly.
Figure 2:
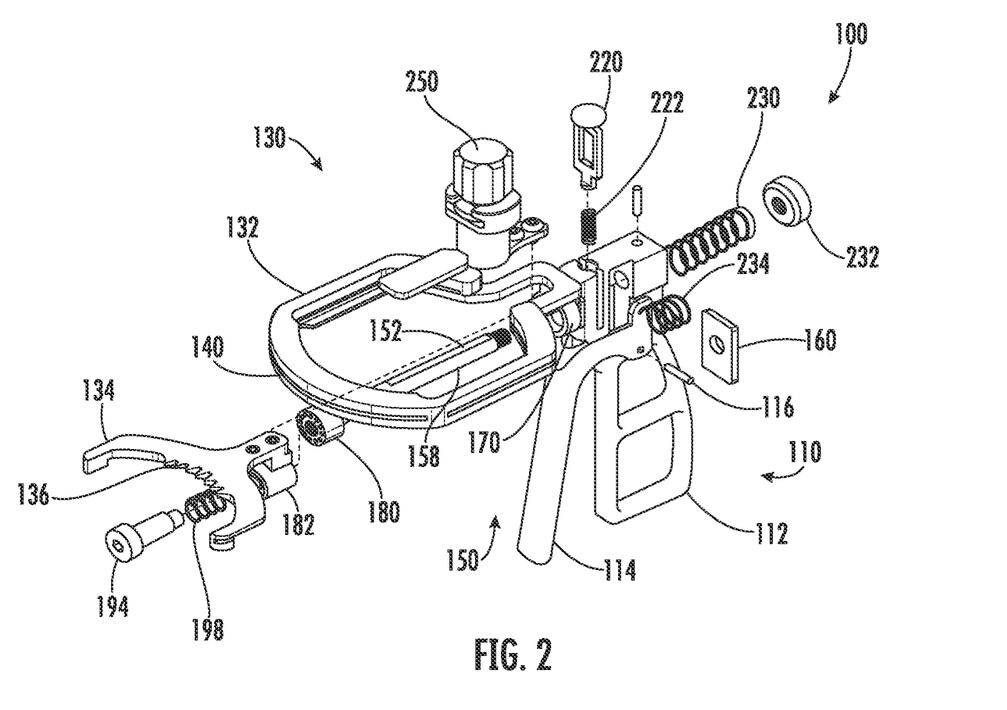
FIG. 2 illustrates an exploded perspective view of the patella clamp shown in FIG. 1.

Referring to FIGS. 1 and 2, an embodiment of a patella clamp 100 in accordance with one or more features of the present disclosure; will now be shown and described. As shown, the patella clamp 100 includes a handle assembly 110 and a clamping assembly 130. As illustrated, in one embodiment, the handle assembly 110 include a first arm 112 and a second arm 114. In one embodiment, the second arm 114 may be moveable and the first arm 112 may be stationary, although other configurations are envisioned such as, for example, where both the first and second arms 112, 114 may be moveable relative to each other. In one embodiment, the second arm 114 may be coupled to the first arm 112 via a pivot pin 116. As will be readily appreciated by one of ordinary skill in the art, thus arranged, in use, a user squeezes the second arm 114 towards the first arm 112 to move, adjust, and/or clamp the clamping assembly 130 about the patient's patella as will be described in greater detail below. As such, as illustrated, the handle assembly 110 may be in the form of a pistol grip, although the handle assembly 110 may be provided in any other suitable mechanisms now known or hereafter developed. As such, the present disclosure should not be limited to any particular type of handle assembly unless explicitly claimed.

Figure 3:
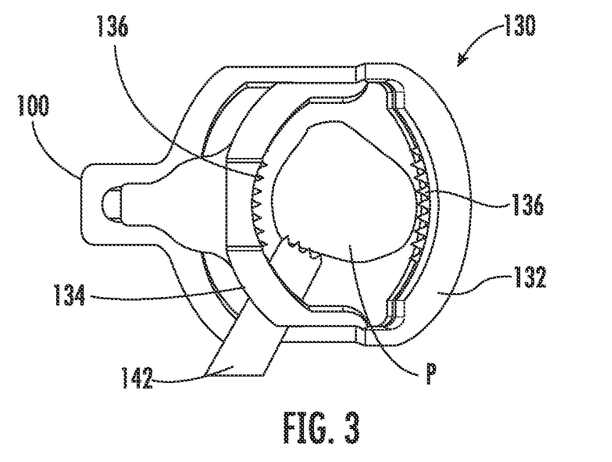
FIG. 3 illustrates a top view of the clamping assembly engaging a patient's patella.
Figure 4:
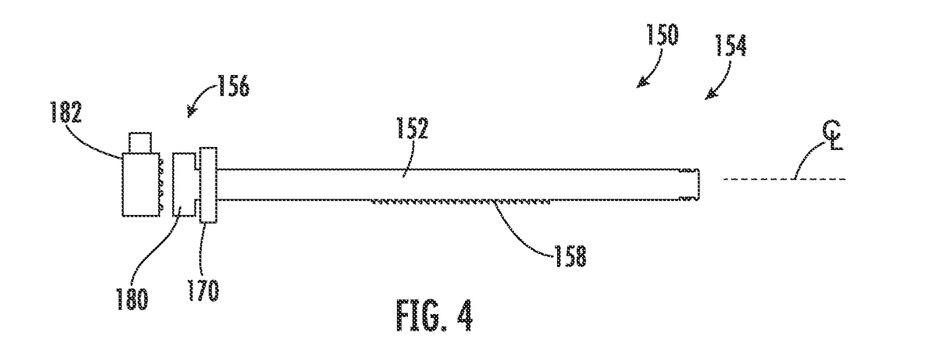
FIG. 4 illustrates a side view of the ratchet arm assembly.
Figure 5:
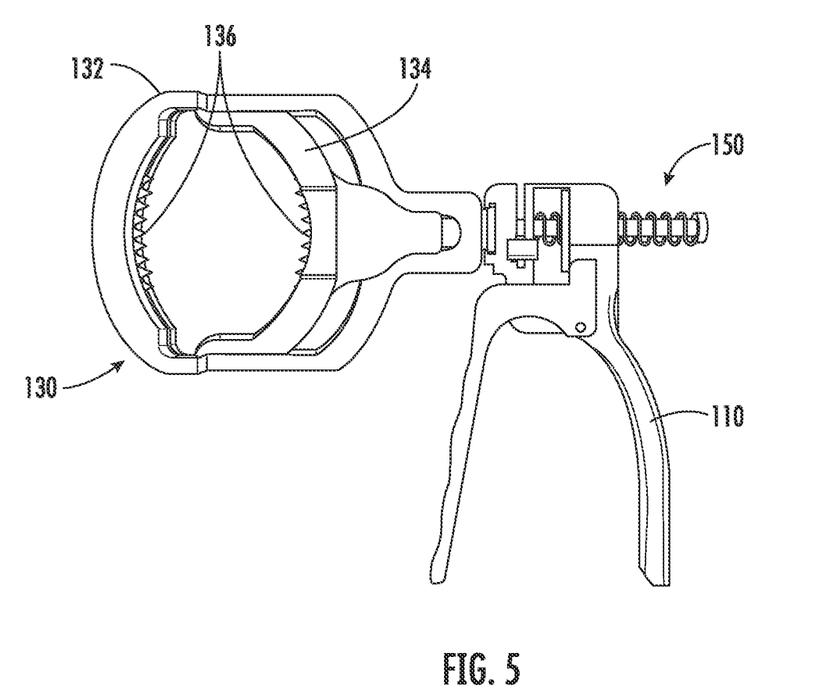
FIG. 5 illustrates a side view of the patella clamp shown in FIG. 1 with the clamping assembly rotated 90 degrees from horizontal.

As illustrated, in one embodiment, the clamping assembly 130 includes a first patella grip portion 132 and a second patella grip portion 134. In one embodiment, the first and second patella grip portions 132, 134 may be arranged and configured in opposing mating relationship with the second patella grip portion 134 moveably positioned relative to the first patella grip portion 132. For example, the second patella grip portion 134 may be arranged and configured to move towards the first patella grip portion 132 via actuation of the handle assembly 110. Thus arranged, with additional reference to FIG. 3, a user can move the second patella grip portion 134 towards the first patella grip portion 132 to capture a patient's patella P positioned therebetween. In addition, in embodiment, as best illustrated in FIGS. 3 and 5, the first and second patella grip portions 132, 134 may include teeth, spikes, serrations, etc. 136 (terms used interchangeably herein without the intent to limit) to capture or grab the patient's patella P. In one embodiment, the first and second patella grip portions 132, 134 may be arranged and configured to provide an opening (e.g., distance between the first and second patella grip portions 132, 134) of approximately 60 mm to grip various sized patellas, although this is but one configuration and other dimensions may be used.

As such, with reference to FIG. 3, in use, the first patella grip portion 132 can hold the patient's patella P using the teeth 136 associated therewith. Thereafter, by actuating the handle assembly 110, the second patella grip portion 134 can be moved towards the patient's patella P to engage the patient's patella P with opposing teeth 136 associated with the second patella grip portion 134. As illustrated, in one embodiment, a sawblade 142 may be inserted from the side of first patella grip portion 132. For example, the sawblade 142 may enter through dedicated cutting slots or may rest on a surface of the first patella grip portion 132. In use, the sawblade 142 may be used to cut or resect a portion of the patient's patella P (e.g., cutting posterior surface of the patient's patella P).

As illustrated, in one embodiment, the handle assembly 110 may be coupled to the clamping assembly 130 by a ratchet arm assembly 150, although it is envisioned that the handle assembly 110 may be coupled to the clamping assembly 130 by other suitable mechanisms now known or hereafter developed. In use, the ratchet arm assembly 150 is arranged and configured to transfer actuation of the handle assembly 110 to the clamping assembly 130 so that, as will be appreciated by one of ordinary skill in the art, actuation of the handle assembly 110 (e.g., user squeezes the first and second arms 112, 114 so that the second arm 114 moves toward the first arm 112), the second patella grip portion 134 is moved towards the first patella grip portion 133 to, for example, engage a patient's patella P positioned therebetween.

In one embodiment, with reference to FIG. 5, the ratchet arm assembly 150 includes a ratchet arm 152 having a first end 154, a second end 156, and a plurality of teeth 158 positioned between the first and second ends 154, 156. The ratchet arm assembly 150 may also include a lever 160 (FIGS. 1 and 2) and a bushing 170. In use, the lever 160 is mounted over the ratchet arm 152 in contact with the teeth 158 formed on the ratchet arm 152. In use, as will be readily appreciated by one of ordinary skill in the art, activation of the handle assembly 110 pushes on a lower portion of lever 160 towards the second end 156 of the ratchet arm 152. The lever 160 sequentially engages and/or interacts with the plurality of teeth 158 on the ratchet arm 152 to translate the ratchet arm 152 distally in the direction of the second end 156.

With reference to FIGS. 1, 2, 4, and 9, the ratchet arm 152 includes an engagement element (e.g., a first engagement element) 180 coupled to or associated with the second end 156 thereof. In use, the engagement element 180 is non-rotatably coupled to the ratchet arm 152 so that the engagement element 180 does not rotate about a longitudinal axis $C_L$ of the ratchet arm 152. Similarly, as illustrated, the second patella grip portion 134 includes an engagement element (e.g., a second engagement element) 182. In use, the first and second engagement elements 180, 182 include mating surfaces 184, 186, respectively. The mating surfaces 184, 186 include mating features 188, 190. In use, the mating features 190 on the mating surface 186 of the second engagement element 182 associated with the second patella grip portion 134 is arranged and configured to couple with the mating features 188 on the mating surface 184 of the first engagement element 160 of the ratchet arm 152.

Figure 9:
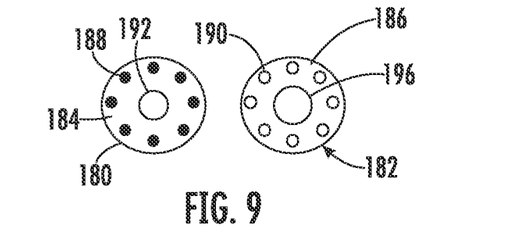
FIG. 9 illustrates an end view of a first engagement element and a second engagement element that may be used in connection with a patella clamp in accordance with one or more features of the present disclosure.

In one embodiment, with reference to FIG. 9, the mating features 188, 190 may be provided as a plurality of corresponding raised features and recessed features arranged and configured to mate with each other (e.g., a plurality of mating male and female protrusions and recesses). For example, as illustrated, the raised features may be semi-spherical in nature, although the exact shape and number of features is not crucial and thus the raised features may be provided in alternate forms such as, but not limited to, mating teeth or the like. Moreover, while eight possible rotational positions are illustrated for the first and second engagement elements 180, 182 when they are mated, this is but one configuration and it is envisioned that more or less raised and recessed features may be provided. Additionally, mating features 188, 190 are not limited to raised features and recessed features and may be provided in any other suitable form now known or hereafter developed including, for example, a Hirth coupling, ball plungers, a splined coupling, or any other type of mechanical linkage or arrangement that allows for selective engagement and rotation of the first and second engagement elements.

For example, in one embodiment, the mating surface 184 of the first engagement element 180 may include a series of detents arranged in a radial pattern. The mating features 190 on the mating surface 186 of the second engagement element 182 may include a series of protrusions arranged in a radial pattern. Alternatively, the detents may be on the second engagement element 180 and the protrusions may be on the first engagement element 182. In use, the protrusions selectively mate with the series of detents to secure a position of the second engagement element 182, and hence the second patella grip portion 134, relative to the ratchet arm 152 and hence the handle assembly 110.

Referring to FIG. 9, in one embodiment, the first engagement element 180 associated with the ratchet arm 152 may include an internally threaded bore 192 to mate with a fastener 194 (FIGS. 1 and 2). As illustrated, the second engagement element 182 associated with the second patella grip portion 134 includes a through-hole 196 arranged and configured to allow the fastener 194 to pass therethrough so that the fastener 194 may threadably engage the threaded bore 192 of the first engagement element 180 of the ratchet arm 152.

As illustrated, in one embodiment, as previously mentioned, the ratchet arm assembly 150 may also include a bushing 170. In use, the bushing 170 is mounted over the ratchet arm 152 (e.g., the bushing 170 includes an opening arranged and configured to allow the ratchet arm 152 to pass therethrough). In use, the bushing 170 is free to rotate about the longitudinal axis $C_L$ of the ratchet arm 152. In addition, the bushing 170 is free to translate relative to the ratchet arm 152. In use, the bushing 170 is coupled to or associated with the first patella grip portion 132. As such, in use, the bushing 170 couples the first patella grip portion 132 to the ratchet arm 152. Thus arranged, in use, actuation of the handle assembly 110 cause the first engagement element 180 and the second engagement element 182 to move distally in the direction of the second end 156 of the ratchet arm 152. In addition, since the second patella grip portion 134 is coupled to the second engagement element 182, the second patella grip portion 134 and optional resection height stylus 250 move distally. However, because the first patella grip portion 132 is coupled to the ratchet arm assembly 150 via the bushing 170, which is free to rotate and translate along the ratchet arm 152, the first patella grip portion 132 remains stationary and does not move relative to ratchet arm 152.

As best illustrated in FIG. 2, the ratchet arm assembly 150 may also include a first biasing element 198 positioned about the fastener 194 between an enlarged head portion of the fastener 194 and the second engagement element 182 associated with the second patella grip portion 134. In this particular embodiment, the fastener 194 retains the first biasing element 198 and the second engagement element 182 on the second end 156 of the ratchet arm 152. Thus arranged, the first biasing element 198, which may be in the form of a coiled spring, biases the second engagement element 182 associated with the second patella grip portion 134 against the first engagement element 180 associated with the ratchet arm 152. In use, a user may grip, hold, etc. the first engagement element 180 and pull on the second engagement element 182 against the bias of the first biasing element 198 so that the mating features 188, 190 on the first and second engagement elements 180, 182 are decoupled or separated (e.g., move the second engagement 182 away from the first engagement element 180 and the handle assembly 110). Thereafter, with the second engagement element 182 separated from the first engagement element 180, the handle assembly 110 can be rotated relative to the first and second patella grip portions 132, 134 (e.g., the clamping assembly 130) about the longitudinal axis $C_L$ of the ratchet arm 152. Once the desired orientation of the first and second patella grip portions 132, 134 (e.g., the clamping assembly 130) is reached, a user may release the second engagement element 182 causing the first biasing element 198 to bias the second engagement element 182 into engagement with the first engagement 180 (e.g., the second engagement element 182 and the first engagement element 180 are biased back together in mating relationship). Thus arranged, with reference to FIG. 5, in accordance with features of the present disclosure, the clamping assembly 130 (e.g., the first and second patella grip portions 132, 134) can be rotated relative to the handle assembly 110. For example, as illustrated, the damping assembly 130 (e.g., the first and second patella grip portions 132, 134) can be oriented at about 90 degrees from horizontal.

Figure 6:
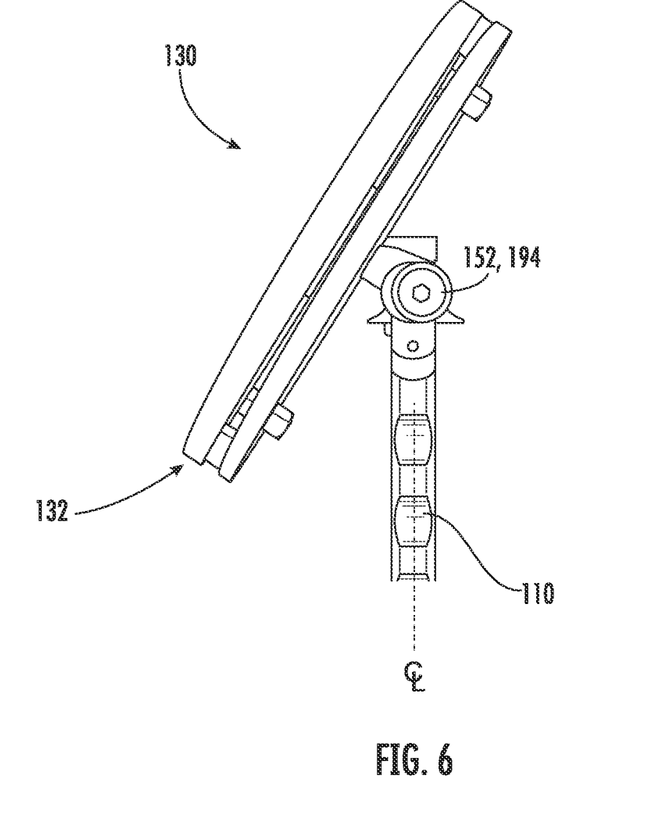
FIG. 6 illustrates an end-view of the patella clamp shown in FIG. 1 with the clamping assembly rotated 45 degrees from horizontal.

In addition, with reference to FIG. 6, by disengaging the second engagement element 182 from the first engagement element 180, the clamping assembly 130 (e.g., the first and second patella grip portions 132, 134) can be rotated, angulated, etc. relative to the longitudinal axis $C_L$ of the ratchet arm 152. As illustrated, for example, the clamping assembly 130 (e.g., the first and second patella grip portions 132, 134) can be oriented at about 45 degrees from longitudinal axis $C_L$ of the ratchet arm 152.

Referring to FIG. 2, in one embodiment, the patella clamp 100 may also include a lock button 220 arranged and configured to interact with the teeth 158 formed on the ratchet arm 152 to fix, hold, secure, etc. a position of the second patella grip portion 134 relative to the first patella grip portion 132. In use, the handle assembly 110 may include a longitudinal bore sized to accept the ratchet arm 152. For example, the first arm 112 of the handle assembly 110 may include a proximal portion and a distal portion, the lock button 220 may be mounted in the proximal portion of the first arm 112 of the handle assembly 110. In use, the first arm 112 may engage the teeth 158 formed on the ratchet arm 152. In addition, as illustrated, the lock button 220 may be biased into engagement with the teeth 158 via a biasing element 222 (e.g., a second biasing element), which may be in the form of a coil spring. In use, as the user actuates the handle assembly 110 (e.g., depresses or squeezes the second arm 114 towards the first arm 112), the ratchet arm 152 is urged distally toward the second end 156 of the ratchet arm 152, the lock button 220 engages the teeth 158 formed on the ratchet arm 152 to fix, secure, hold, etc. the position of the ratchet arm 152 (e.g., to fix, secure, hold, etc. a position of the second patella grip portion 134 relative to the first patella grip portion 132). In addition, the biasing element 222 engages or biases the lock button 220 with the teeth 158 formed on the ratchet arm 152 causing an audible clicking noise as feedback to the user as the teeth 158 formed on the ratchet arm 152 advance over lock button 220. Thereafter, in use, where the user desires to release or open the clamping assembly 130 to, for example, release the patient's patella from in-between the first and second patella grip portions 132, 134, the user depresses the lock button 220 against the bias of the biasing element 222 causing the lock button 220 to disengage from the teeth 158 formed on the ratchet arm 152. Thereafter, as will be described below, a biasing element 230 may move or bias the clamping assembly 130 in a non-clamping position (e.g., depressing the lock button 220 disengages the lock button 220 from the ratchet arm 152 so that the second patella grip portion 134 may be moved relative to the first patella grip portion 132 to, for example, release the patient's patella from in-between the first and second patella grip portions 132, 134).

In addition, with reference to FIG. 2 and as previously mentioned, the patella clamp 100 may include a biasing element 230 (e.g., a third biasing element) located adjacent to the first end 154 of the ratchet arm 152. In use, as the ratchet arm 152 is urged distally in the direction of the second end 156, the biasing element 230 is compressed thus providing resistance to the user. In use, when the user depresses the lock button 220, the lock button 220 disengages from the ratchet arm 152, the biasing element 230 moves or biases the clamping assembly 130 in a non-clamping position (e.g., biases the second patella grip portion 134 away from the first patella grip portion 132 to, for example, release the patient's patella from in-between the first and second patella grip portions 132, 134). As illustrated, in one embodiment, the biasing element 230 may be in the form of a compression spring, however other biasing elements may be used such as, for example, a spring, an elastomeric washer, a Bellville washer, or any and all biasing elements known or contemplated. In use, the biasing element 230 may be held onto the ratchet arm 152 with a nut 232.

In addition, the patella clamp 100 may also include an additional biasing element (e.g., a coiled compression spring or the like) 234. The biasing element 234 may be mounted over the ratchet arm 152 adjacent to the lever 160. In use, the biasing element 234 is arranged and configured to bias the lever 160 towards the first end 154 of the ratchet arm 152 and prevents movement of the lever 160 unless the second arm 114 of the handle assembly 110 is actuated.

Referring to FIGS. 1 and 2, in one embodiment, the first patella grip portion 132 may include a cutting slot 140. As illustrated, the cutting slot 140 may extend circumferentially about the first patella grip portion 132 (e.g., the cutting slot 140 may extend around a perimeter of first patella grip portion 132). For example, the cutting slot 140 may extend approximately 270 degrees, although this is but one example embodiment and the cutting slot 140 may extend more or less. In use, the cutting slot 140 is arranged and configured to receive a sawblade 142 (FIG. 4) to resect a portion of the patent's patella.

Figure 7:
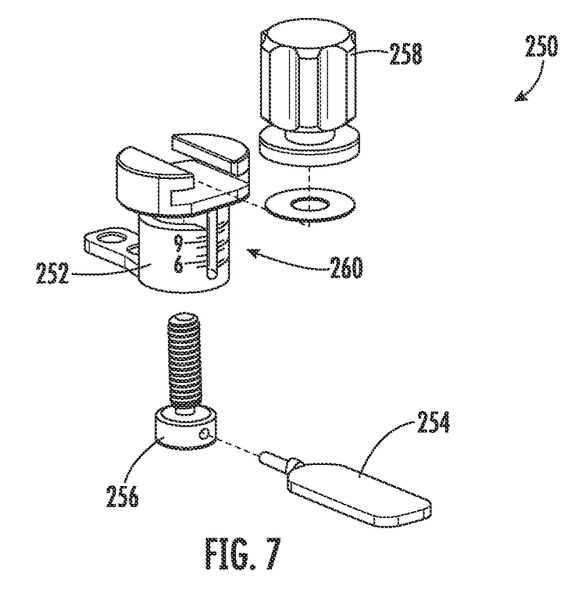
FIG. 7 illustrates an exploded perspective view of an embodiment of a resection height stylus that may be used in connection with a patella clamp in accordance with one or more features of the present disclosure.

In addition, and/or alternatively, in one embodiment, the patella clamp 100 may also include a resection height stylus 250. In use, the optional resection height stylus 250 may be releasably coupled to the second patella grip portion 134 and when used in combination with the cutting slot 140 may assist a surgeon in determining how much of the patient's patella to resect. That is, referring to FIGS. 1, 2, and 7, in one embodiment, the patella clamp 100 may include a resection height stylus 250. In use, the resection height stylus 250 may be coupled to the second patella grip portion 134. As best illustrated in FIG. 7, the resection height stylus 250 includes a resection body 252 and a paddle 254. The paddle 254 may be received within a bolt 256, which may be received within a bore formed in the resection body 252. The resection height stylus 250 may also include a knob 258 coupled to the resection body 252 and the bolt 256. As illustrated, in one embodiment, the bolt 256 may include a shaft portion including external threads. In use, the shaft portion is arranged and configured to extend through the bore formed in the resection body 252 and into engagement with internal threads formed in a bore of the knob 258 so that rotation of the knob 258 adjusts the height of the resection height stylus 250. Thus arranged, in use, with a patient's patella clamped between the first and second patella grip portions 132, 134 of the clamping assembly 130, the surgeon may assess the patient's patella including, for example, determining how much bone to resect. Thereafter, the surgeon may adjust the resection height by rotating the knob 258, which raises and/or lowers the height of paddle 254 and thus adjusts the amount of resection.

In one embodiment, the resection height stylus 250 may also include resection indicia 260. Thus arranged, with the paddle 254 positioned in contact with the patella's patella and with the patella clamped, the resection indicia 260 displays to the surgeon the amount of resection (e.g., the indicia 260 can provide an indication of how much of the patient's patella will be removed with a saw). In one embodiment, the indicia 260 may indicate in millimeters how much of the patient's patella will be removed with a saw.

Figure 8:
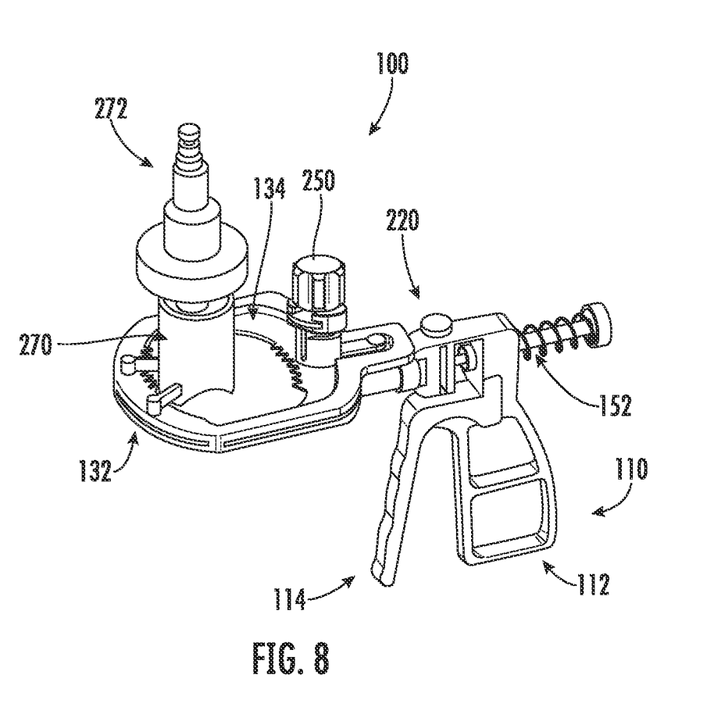
FIG. 8 illustrates a perspective view of an alternate embodiment of a patella clamp in accordance with one or more features of the present disclosure, the patella clamp including a reaming guide.

In addition, and/or alternatively, in one embodiment, the patella clamp 100 may be arranged and configured to engage a patella reamer guide. As illustrated, in FIG. 8, in one embodiment, the patella clamp 100 may be arranged and configured to engage a patella reamer guide 270. For example, in one embodiment, the patella reamer guide 270 may be coupled to the first patella grip portion 132. In use, the patella reamer guide 270 may be coupled to the first patella grip portion 132 by any suitable mechanism now known or hereafter developed. In use, with a patient's patella gripped by the first and second patella grip portions 132, 134 of the patella clamp 100, the patella reamer guide 270 may be coupled to the patella clamp 100 and a reamer 272 can be inserted into the patella reamer guide 270 and a driver (not shown) can rotate the reamer 272 to remove portions of the patient's patella. Thus arranged, the patella clamp 100 is arranged and configured to assist surgeons with visualization of the patient's knee (e.g., orientation of reaming). That is, in use, the patella clamp 100 enables the surgeon to visualize the plane where cutting (e.g., reaming) can be performed. Thereafter, by setting or coupling the patella reamer guide 270 to the clamping assembly 130, the surgeon is better able to create the desired reaming plane.

The foregoing description has broad application. While the present disclosure refers to certain embodiments, numerous modifications, alterations, and changes to the described embodiments are possible without departing from the sphere and scope of the present disclosure, as defined in the appended claim(s). Accordingly, it is intended that the present disclosure not be limited to the described embodiments. Rather these embodiments should be considered as illustrative and not restrictive in character. All changes and modifications that come within the spirit of the invention are to be considered within the scope of the disclosure. The present disclosure should be given the full scope defined by the language of the following claims, and equivalents thereof. The discussion of any embodiment is meant only to be explanatory and is not intended to suggest that the scope of the disclosure, including the claims, is limited to these embodiments. In other words, while illustrative embodiments of the disclosure have been described in detail herein, it is to be understood that the inventive concepts may be otherwise variously embodied and employed, and that the appended claims are intended to be construed to include such variations, except as limited by the prior art. Unless otherwise defined, all technical terms used herein have the same meaning as commonly understood by one of ordinary skill in the art to which the disclosure belongs.

Directional terms such as top, bottom, superior, inferior, medial, lateral, anterior, posterior, proximal, distal, upper, lower, upward, downward, left, right, longitudinal, front, back, above, below, vertical, horizontal, radial, axial, clockwise, and counter-clockwise) and the like may have been used herein. Such directional references are only used for identification purposes to aid the reader's understanding of the present disclosure. For example, the term "distal" may refer to the end farthest away from the medical professional/operator when introducing a device into a patient, while the term "proximal" may refer to the end closest to the medical professional when introducing a device into a patient. Such directional references do not necessarily create limitations, particularly as to the position, orientation, or use of this disclosure. As such, directional references should not be limited to specific coordinate orientations, distances, or sizes, but are used to describe relative positions referencing particular embodiments, Such terms are not generally limiting to the scope of the claims made herein. Any embodiment or feature of any section, portion, or any other component shown or particularly described in relation to various embodiments of similar sections, portions, or components herein may be interchangeably applied to any other similar embodiment or feature shown or described herein.

It should be understood that, as described herein, an "embodiment" (such as illustrated in the accompanying Figures) may refer to an illustrative representation of an environment or article or component in which a disclosed concept or feature may be provided or embodied, or to the representation of a manner in which just the concept or feature may be provided or embodied. However, such illustrated embodiments are to be understood as examples (unless otherwise stated), and other manners of embodying the described concepts or features, such as may be understood by one of ordinary skill in the art upon learning the concepts or features from the present disclosure, are within the scope of the disclosure. Furthermore, references to "one embodiment" of the present disclosure are not intended to be interpreted as excluding the existence of additional embodiments that also incorporate the recited features.

In addition, it will be appreciated that while the Figures may show one or more embodiments of concepts or features together in a single embodiment of an environment, article, or component incorporating such concepts or features, such concepts or features are to be understood (unless otherwise specified) as independent of and separate from one another and are shown together for the sake of convenience and without intent to limit to being present or used together. For instance, features illustrated or described as part of one embodiment can be used separately, or with another embodiment to yield a still further embodiment. Thus, it is intended that the present subject matter covers such modifications and variations as come within the scope of the appended claims and their equivalents.

As used herein, an element or step recited in the singular and proceeded with the word "a" or "an" should be understood as not excluding plural elements or steps, unless such exclusion is explicitly recited. It will be further understood that the terms "comprises" and/or "comprising," or "includes" and/or "including" when used herein, specify the presence of stated features, regions, steps, elements and/or components, but do not preclude the presence or addition of one or more other features, regions, integers, steps, operations, elements, components and/or groups thereof.

The phrases "at least one", "one or more", and "and/or", as used herein, are open-ended expressions that are both conjunctive and disjunctive in operation. The terms "a" (or "an"), "one or more" and "at least one" can be used interchangeably herein.

Connection references engaged, attached, coupled, connected, and joined) are to be construed broadly and may include intermediate members between a collection of elements and relative to movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another. The drawings are for purposes of illustration only and the dimensions, positions, order and relative to sizes reflected in the drawings attached hereto may vary.

The foregoing discussion has been presented for purposes of illustration and description and is not intended to limit the disclosure to the form or forms disclosed herein. For example, various features of the disclosure are grouped together in one or more embodiments or configurations for the purpose of streamlining the disclosure. However, it should be understood that various features of the certain embodiments or configurations of the disclosure may be combined in alternate embodiments or configurations. Moreover, the following claims are hereby incorporated into this Detailed Description by this reference, with each claim standing on its own as a separate embodiment of the present disclosure.

The invention claimed is:

1. A patella clamp comprising:
   a clamping assembly including first and second patella grip portions;
   a handle assembly including a first arm and a second arm; and
   a ratchet arm assembly arranged and configured to couple the handle assembly to the clamping assembly so that actuation of the handle assembly is transferred to the clamping assembly to secure a patient's patella between the first and second patella grip portions;
   wherein the ratchet arm assembly is arranged and configured to enable the handle assembly to rotate around a longitudinal axis of the ratchet arm assembly so that a position of the handle assembly can be adjusted relative to the clamping assembly.

2. The patella clamp of claim 1, wherein the ratchet arm assembly includes:
   a ratchet arm having a first end operably associated with the handle assembly and a second end operably associated with the clamping assembly; and
   a first engagement element coupled to the second end, the first engagement element being non-rotatably coupled to the ratchet arm;
   wherein the second patella grip portion includes:
      a second engagement element selectively engageable with the first engagement element, and
      a biasing element to bias the second engagement element to couple with the first engagement element,
   wherein coupling of the second engagement element with the first engagement element prevents rotation of the handle assembly.

3. The patella clamp of claim 2, wherein, in use, separating the second engagement element from the first engagement element enables the clamping assembly to be rotated relative to the handle assembly.

4. The patella clamp of claim 3, wherein the ratchet arm assembly further comprises a bushing moveably coupled to the ratchet arm, the bushing operably coupled to the first patella grip portion to moveably couple the first patella grip portion to the ratchet arm.

5. The patella clamp of claim 4, wherein the ratchet arm assembly further comprises a fastener passing through a bore formed in the second engagement element and into threaded engagement with a threaded bore formed in the first engagement element to couple the second engagement element and the second patella grip portion to the ratchet arm.

6. The patella clamp of claim 5, wherein the biasing element is positioned between a head of the fastener and the second engagement element.

7. The patella clamp of claim 3, wherein the first and second engagement elements each include a mating surface and a mating feature arranged and configured to engage a mating feature of the other engagement element.

8. The patella clamp of claim 7, wherein the mating feature comprises a plurality of corresponding male protrusions and female recesses arranged and configured to mate with each other.

9. The patella clamp of claim 2, wherein the ratchet arm further comprises a plurality of teeth positioned between the first and second ends, the ratchet arm assembly including a lever operably associated with the handle assembly such that actuation of the handle assembly causes the lever to interact with the teeth to move the ratchet arm distally to move the first and second patella grip portions relative to each other.

10. The patella clamp of claim 1, wherein the clamping assembly is also arranged and configured to be angulated relative to a longitudinal axis of the ratchet arm.

11. The patella clamp of claim 1, wherein the first and second patella grip portions are arranged and configured in opposing mating relationship, the first patella grip portion being stationary, the second patella grip portion being moveable so that actuation of the handle assembly moves the second patella grip portion towards the first patella grip portion.

12. The patella clamp of claim 1, wherein the second arm is pivotably coupled to the first arm so that movement of the second arm relative to the first arm actuates the handle assembly.

13. The patella clamp of claim 12, wherein the handle assembly is configured as a pistol grip.

14. The patella clamp of claim 1, further comprising a resection height stylus releasably coupled to the second patella grip portion, the resection height stylus being arranged and configured to measure an amount of a patient's bone to be resected.

15. The patella clamp of claim 14, wherein the resection height stylus includes:
 a knob;
 a resection body including a bore formed therein;
 a paddle arranged and configured to contact a patient's patella; and
 a bolt arranged and configured to pass through the bore formed in the resection body and into threaded engagement with the knob, the bolt being coupled to the paddle, in use, rotation of the knob adjusts a position of the paddle relative to the resection body.

16. The patella clamp of claim 1, further comprising a patella reamer guide arranged and configured to receive and guide a reamer, the patella reamer guide being releasably coupled to the first patella grip portion.

17. The patella clamp of claim 1, wherein movement of the second engagement element against the bias of the biasing element causes movement of the second engagement element to a decoupled position to decouple the second engagement element from the first engagement element to allow for rotation of the handle assembly with respect to the clamping assembly.

18. The patella clamp of claim 17, wherein release of the second engagement element from the decoupled position allows the biasing element to bias the second engagement element to couple to the first engagement element to prevent rotation of the handle assembly.

19. A patella clamp comprising:
 a clamping assembly including first and second patella grip portions;
 a handle assembly including first and second arms;
 a ratchet arm assembly arranged and configured to couple the handle assembly to the clamping assembly so that actuation of the handle assembly is transferred to the clamping assembly to move the second patella grip portion relative to the first patella grip portion to secure a patient's patella between the first and second patella grip portions; and
 means for rotatably adjusting the handle assembly relative to the clamping assembly, wherein the handle assembly is configured to rotate around a longitudinal axis of the ratchet arm assembly.

20. The patella clamp of claim 19, wherein the ratchet arm assembly includes:
 a ratchet arm having a first end operably associated with the handle assembly and a second end operably associated with the clamping assembly; and
 the means for rotatably adjusting the handle assembly relative to the clamping assembly includes:
  a first engagement element coupled to the second end, the first engagement element being non-rotatably coupled to the ratchet arm; and
  a second engagement element operably associated with the second patella grip portion, the second engagement element selectively engageable with the first engagement element, wherein, in use, separating the second engagement element from the first engagement element enables the clamping assembly to be rotated relative to the handle assembly.

* * * * *